United States Patent [19]

Kirchmayr et al.

[11] 4,061,604

[45] Dec. 6, 1977

[54] FLAMEPROOFING OF PLASTICS

[75] Inventors: Rudolf Kirchmayr, Aesch; Hugo Illy, Reinach, both of Switzerland

[73] Assignee: Ciba-Geigy Corporation, Ardsley, N.Y.

[21] Appl. No.: 640,992

[22] Filed: Dec. 15, 1975

[30] Foreign Application Priority Data

Dec. 18, 1974 Switzerland .................. 16895/74
Nov. 11, 1975 Switzerland .................. 14565/75

[51] Int. Cl.$^2$ ..................... C07F 9/28; C08K 5/53
[52] U.S. Cl. ................. 260/2.5 AJ; 260/2.5 EP; 260/2.5 FP; 260/45.8 R; 260/47 EP; 260/77.5 SS; 260/927 R
[58] Field of Search ...................... 260/45.8 R, 260/2.5 AJ, 2.5 AM, 47 EP, 47 EC, 927 R, 2.5 EP, 2.5 FP

[56] References Cited

U.S. PATENT DOCUMENTS

| | | | |
|---|---|---|---|
| 3,328,319 | 6/1967 | Galinke et al. | 260/2 |
| 3,490,940 | 1/1970 | Cummins | 260/927 R |
| 3,812,218 | 5/1974 | Golborn et al. | 260/926 |
| 3,812,219 | 5/1974 | Clovis et al. | 260/936 |
| 3,873,496 | 3/1975 | Hills | 260/45.8 R |
| 3,883,478 | 5/1975 | Gresham | 260/45.8 R |
| 3,905,922 | 9/1975 | Smith et al. | 260/2.5 AJ |
| 3,970,635 | 7/1976 | Lawton et al. | 260/45.8 R |
| 3,970,726 | 7/1976 | Batorewicz | 260/927 R |
| 4,002,580 | 1/1977 | Russo | 260/2.5 AJ |

*Primary Examiner*—Donald E. Czaja
*Assistant Examiner*—R. A. White
*Attorney, Agent, or Firm*—Luther A. R. Hall

[57] ABSTRACT

3-Hydroxy-5-phosphono-1,2-oxapholanes can be synthesized from β-dicarbonyl compounds by reaction with 2 moles of an diorganophosphite. The products are usable as flameproofing agents for plastics, particularly for polyurethanes and epoxide resins which are able to react with the hydroxyl group of the oxapholanes.

11 Claims, No Drawings

FLAMEPROOFING OF PLASTICS

The invention relates to a process for the flameproofing of plastics, as well as to the organic phosphorus compounds used for the purpose and to a process for the production of these compounds.

It is known that combustible plastics can be made noncombustible or difficultly combustible by the addition of organic phosphorus compounds.

A particularly difficult problem is the flameproofing of foam plastics made from combustible plastics, because these, by virtue of their porous structure, are more easily ignitable and more readily combustible than compact plastics materials. Foam plastics require therefore greater amounts of the flameproofing agent, a factor having a disadvantageous effect on the mechanical properties of these materials. In the field of foam plastics, therefore, particularly effective flameproofing agents are necessary so that small amounts are sufficient to obtain the desired degree of flameproofing. Especially effective phosphorus compounds that have become known are halogen-containing phosphorus esters, such as are described, for example, in the USA Patent Specifications Nos. 3,014,956, 3,042,701 and 3,192,242. Such halogencontaining phosphorus compounds have however the disadvantage that with the occurrence of fire they split off toxic and corrosive gases.

It has been found that the preferred 3-hydroxy-2-oxo-2-alkoxy 1,2-oxaphospholane-5-phosphonic acid esters are highly effective as flameproofing agents for combustible plastics yet do not have, since they are free from halogens, the aforementioned disadvantage. Furthermore, these flameproofing agents can be incorporated by means of their hydroxyl groups into polymers having reactive groups, with the result that losses due to volatility are avoided.

The invention relates therefore to a process for the flameproofing of combustible plastics, which process comprises incorporating into the plastics 2 to 30 per cent by weight of a compound of the formula I

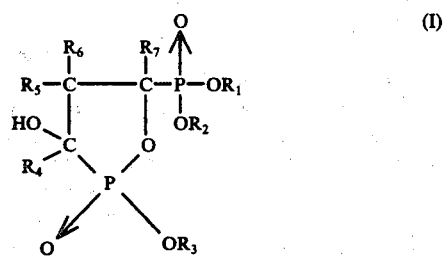

wherein $R_1$ and $R_2$ each independently represent alkyl having 1 - 4 carbon atoms, cyclohexyl, aralkyl having 7 or 8 carbon atoms, halogenoalkyl having 2 - 3 carbon atoms, alkoxyalkyl having 3 - 6 carbon atoms or alkenyl having 3 - 5 carbon atoms, $R_3$ is identical to $R_1$ or $R_2$, $R_4$ is alkyl having 1 - 4 carbon atoms or phenyl, $R_5$ and $R_6$ each independently represent hydrogen or alkyl having 1 - 4 carbon atoms, and $R_7$ represents hydrogen, alkyl having 1 - 4 carbon atoms, alkoxy having 1 - 4 carbon atoms, or phenyl.

The substituents $R_1$ to $R_7$ as alkyl having 1 - 4 carbon atoms can denote methyl, ethyl, propyl, isopropyl, n-butyl, sec.-butyl or tert.-butyl.

As aralkyl having 7 or 8 carbon atoms, $R_1$ to $R_3$ can denote benzyl, methylbenzyl or phenylethyl.

As alkoxyalkyl having 3 to 6 carbon atoms, $R_1$ to $R_3$ can be, for example, methoxyethyl, ethoxyethyl, isopropoxyethyl or butoxyethyl; and as alkenyl having 3 - 5 carbon atoms, the same substituents can be allyl, methallyl or dimethallyl.

As halogenoalkyl, $R_1$ to $R_3$ are, for example, 2-fluoroethyl, 2-chloroethyl, 2-bromoethyl or 2-chloropropyl.

As alkoxy, $R_7$ can be, for example, methoxy, ethoxy, isopropoxy or butoxy.

The compounds of formula I preferably used are those wherein $R_1$ and $R_2$ independently represent alkyl having 1 - 4 carbon atoms, cyclohexyl, benzyl, allyl or alkoxyethyl having 3 - 5 carbon atoms, $R_3$ is identical to $R_1$ or $R_2$, $R_4$ and $R_7$ each independently represent alkyl having 1 - 4 carbon atoms or phenyl, and $R_5$ and $R_6$ represent hydrogen.

Preferably used compounds of formula I are also those wherein $R_1$ and $R_2$ have the same meaning.

The following compounds are examples of compounds of the formula I that are usable according to the invention:

2-oxo-2-ethoxy-3,5-dimethyl-3-hydroxy-5-diethylphosphono 1,2-oxaphospholane, 2-oxo-2-ethoxy-3-phenyl-5-methyl-3-hydroxy-5-diethylphosphono-1,2-oxaphospholane, 2-oxo-2-methoxy-3,5-dimethyl-3-hydroxy-5-dimethylphosphono 1,2-oxaphospholane, 2-oxo-2-isopropoxy-3,5-dimethyl-3-hydroxy-5-diisopropylphosphono-1,2-oxaphospholane, 2-oxo-2-benzyloxy-3,5-dimethyl-3-hydroxy-5-dibenzylphosphono 1,2-oxaphospholane, 2-oxo-2-allyloxy-3,5-dimethyl-3-hydroxy-5-diallylphosphono 1,2-oxaphospholane, 2-oxo-2-methoxyethyloxy-3,5-dimethyl-3-hydroxy-5-di-(methoxyethyl)phosphono-1,2-oxaphospholane, 2-oxo-2-β-chloroethyloxy-3,5-dimethyl-3-hydroxy-5-di-(β-chloroethyl)phosphono-1,2-oxaphospholane, 2-oxo-2-ethoxy-3,4,5-trimethyl-3-hydroxy-5-diethylphosphono-1,2-oxaphospholane, 2-oxo-2-methoxy-3,5-dimethyl-4,4-diethyl-3-hydroxy-5-dimethylphosphono-1,2-oxaphospholane, 2-oxo-2-ethoxy-3-methyl-3-hydroxy-5-diethylphosphono-1,2-oxaphospholane, 2-oxo-2-ethoxy-3,5-diisobutyl-3-hydroxy-5-diethylphosphono-1,2-oxaphospholane, 2-oxo-2-ethoxy-3-methyl-3-hydroxy-5-ethoxy-5-diethylphosphono-1,2-oxaphospholane, 2-oxo-2-methoxy-3-phenyl-3-hydroxy-5-methoxy-5-dimethylphosphono-1,2; -oxaphospholane.

The described process is suitable as a flameproofing process for all combustible plastics, for example for homo- or copolymers of α-olefins, styrene, 1,3-dienes, of vinyl acetate, acrylic or methacrylic esters or of acrylonitrile; also for polycondensation products such as polyesters, polyamides, polycarbonates or polyethers. Of great importance, in addition to the flameproofing of these thermoplastics, is also the flameproofing of curable resins, such as polyester resins, phenol resins or alkyd resins; the described process is particularly suitable for polyurethanes and epoxide resins.

The process is of particular interest for the flameproofing of foamed plastics made from combustible materials, especially for foamed plastics from polyurethanes.

The addition of the flameproofing agent to the individual plastics can be made during production of the polymer, with a very homogeneous distribution being ensured. The flameproofing agent may however also be mixed with the polymer, for example when this is in the granulated or pulverised form. If the plastics material is produced from two reactive constituents, such as in the case of polyurethanes or epoxide resins, then the flameproofing agent is advantageously firstly premixed with the constituent which does not react with hydroxyphospholane derivatives of the formula I. In the production of polyurethanes, therefore, the hyroxyphospholane derivative is advantageously initially mixed with the polyol constituent in order to avoid a premature reaction of the isocyanate constituent with the flameproofing agent. On mixing of the two constituents, the isocyanate groups react with the hydroxyl groups both of the polyol constituent and of the hydroxyphospholane derivative, in consequence of which there occurs a chemical bonding of the flameproofing agent into the polyurethane plastics.

In addition to the flameproofing agents of the formula I, there can be added to the plastics other known flameproofing agents such as organic halogen compounds, on their own or in combination with antimony oxide, or other phosphorus compounds. There can moreover be used, besides the flameproofing agents, additives customarily employed in the plastics industry, such as pigments, fillers, plasticisers, antistatic agents, lubricants, antioxidants, light stabilisers or other stabilisers.

The amount of flameproofing agent added is governed by the degree of flameproofing desired as well as by the combustibility of the substrate. In general, there is used 2 to 30 per cent by weight, preerably 4 to 15 per cent by weight.

The plastics mixed with the flameproofing agent can be processed into the form of films, fibres, foam plastics, hollow shapes, sheets, sections or other moulded articles, for which the various known moulding processes can be used, such as extruding, rolling, pressing, spinning, blow moulding or injection moulding. Foam plastics products can be produced by expanding polymeric material, or during the formation of the polymer. In both cases, the flameproofing agent is added before the expanding operation.

The compounds of the formula I are new compounds with the exception of the compound of the formula I wherein $R_1$, $R_2$ and $R_3$ represent ethyl, $R_4$ and $R_7$ methyl and $R_5$ and $R_6$ hydrogen. This compound is known, without any reference to a flameproofing effect, from B. A. Arbusov, et. al, Bull.Acad. Sci. USSR, Div.Chem.-Sci., Vol. 12 (1971), 2757-2761.

The invention relates therefore also to the compounds of the formula I wherein $R_1$ and $R_2$ each independently represent methyl, propyl, butyl, cyclohexyl, aralkyl having 7 or 8 carbon atoms, alkoxyalkyl having 3 – 6 carbon atoms, halogenoalkyl having 2 – 3 carbon atoms, or alkenyl having 3 – 5 carbon atoms, $R_3$ is identical to $R_1$ or $R_2$, $R_4$ is alkyl having 1 – 4 carbon atoms or pheny, $R_5$ and $R_6$ each independently represent hydrogen or alkyl having 1 – 4 carbon atoms, and $R_7$ represents hydrogen, alkyl having 1 – 4 carbon atoms, alkoxy having 1 – 4 carbon atoms or phenyl.

A further subject of the invention is a process for the production of compounds of the formula I, wherein $R_1$ and $R_2$ each independently represent alkyl having1 – 4 carbon atoms, cyclohexyl, aralkyl having 7 or 8 carbon atoms, alkoxyalkyl having 3 – 6 carbon atoms, halogenoalkyl having 2 – 3 carbon atoms, or alkenyl having 3 – 5 carbon atoms, $R_3$ is identical to $R_1$ or $R_2$, $R_4$ is alkyl having 1 – 4 carbon atoms or phenyl, $R_5$ and $R_6$ each independently represent hydrogen or alkyl having 1 – 4 carbon atoms, and $R_7$ represents hydrogen, alkyl having 1 – 4 carbon atoms, alkoxy having 1 – 4 carbon atoms or phenyl, by reaction of a dicarbonyl compound of the formula II

with at least 2 molar equivalents of a diorganophosphite of the formula $(R_1O)(R_2O)POH$ in the presence of a basic catalyst, in which process the reaction is performed in an inert solvent and at elevated temperature.

Examples of dicarbonyl compounds of the formula II are- acetylacetone, 3-methyl-acetylacetone, 3,3-diethylacetylacetone, benzoylacetone, dibenzoylmethane, 1,1dibenzoylethane, acetylacetaldehyde (butanedione-2,4), propionylacetone (hexanedione-2,4)isobutyrylacetone(5,5-dimethyl-hexanedione-2,4), and methyl, ethyl or butyl esters of acetoacetic acid and benzoylacetic acid.

There can be used diorganophosohites wherein $R_1$ and $R_2$ are identical, such as dimethyl-, diethyl-, di-isopropyl-, di-sec.-butyl-, dicyclohexyl-, dibenzyl-, di-($\beta$-methoxyethyl)-, di($\beta$-chloroethyl)- or dimethallylphosphite. There can however also be used phosphites which have two different ester groups, such as methylethyl-phosphite, methyl-butyl-phosphite or propylallyl-phosphite. At least 2 moles, preferably 2.2 to 3 moles, of phosphite are used per mole of the dicarbonyl compound. The unreacted phosphite is recovered in the processing by distillation.

Suitable solvents are, in particular, hydrocarbons such as benzene, toluene, xylene, ligroin, heptane or cyclohexane. Also suitable are solvents of ether type such as diethyl ether, di-isopropyl ether, tetrahydrofuran, dioxane or 1,2-dimethoxyethane.

Basic catalysts suitable for the reaction are alkali metals or alkaline-earth metals as well as hydrides, amides or alcoholates thereof. In some cases it is advantageous to add further amounts of the base in the course of the reaction.

The reaction is advantageously performed at a temperature of 50° to 120° C, preferably at 75° to 95° C.

The reaction can be performed by dissolving the dicarbonyl compound in the solvent and adding, whilst heating, a part of the phosphite as well as the catalyst. After commencement of the reaction, there are then added the remainder of the phosphite and, if necessary, a further amount of catalyst. Another method of reaction is to place the phosphite together with the catalyst and the solvent, and to add the dicarbonyl compound dropwise with heating.

A further embodiment comprises firstly mixing the dicarbonyl compound with the phosphite and the solvent, adding the catalyst, and then completing the reaction by heating.

The isolation of the oxaphospholane derivatives can be effected by conventional methods, preferably by distilling off the solvent and the unreacted phosphite. Before distillation, the basic catalyst is advantageously neutralised by the addition of an acid.

In the Bull. Acad. Sci. USSR, Div. Chem. Sci., Vol. 12 (1971), pages 2757-2761, there is described the reaction of acetylacetone with two molar equivalents of diethylphosphite at room temperature without the use of a solvent, for which reaction a solution of NaOC₂H₅ in ethanol is used as catalyst. As the reaction product there is obtained 2-oxo-2-ethoxy-3,5-dimethyl-3-hydroxy-5-diethylphosphono-1,2-oxaphospholane in relatively low yield. In contrast to this process, the process of the invention produces the corresponding oxaphospholane derivatives in high yields and in a substantially shorter reaction time, and is therefore suitable for commercial application.

The following Examples describe further the new process for the production of 3-hydroxy-2-oxo-2-alkoxy-1,2-oxaphospholane-5-phosphonic acid esters and the use thereof as flameproofing agents for plastics. The term 'parts' denotes therein parts by weight and % percentages by weight.

EXAMPLE 1

100 parts (1 mole) of acetylacetone in 265 parts of absolute benzene are stirred with 20 parts of diethylphosphite at 80°. After the addition of 0.4 part of sodium, there are slowly added dropwise within 2 hours, with gentle boiling, 330 parts of diethylphosphite (total 2.4 moles), with the pH-value being maintained with 2 parts of sodium at between 8 and 10. After completion of the dropwise addition, the reaction mixture is stirred for a further half hour. After cooling to room temperature, the mixture is neutralised with glacial acetic acid; it is filtered off from any precipitate present and the solvent is removed in vacuo. The unreacted diethylphosphite is distilled off at 0.01 mm and at a maximum bath temperature of 100° C.

There remain 284 parts of 2-oxo-2-ethoxy-3,5-dimethyl-3-hydroxy-5-diethylphosphono-1,2-oxaphospholane as viscous oil. This corresponds to a yield of 86% Elementary analysis $C_{11}H_{24}O_7P_2$

| calculated | C 40% | H 7.27% | P 18.78% |
|---|---|---|---|
| found | 39.8% | 7.33% | 18.59% |

Molecular weight according to mass spectrum: 330 (cal. 330); ethoxy content: cal. = 40.8%, found = 39.5%.

The infra-red spectrum displays characteristic bands for the hydroxyl group at 3300 cm⁻¹ and for the P → O-groups at 1225 and 1275 cm⁻¹.

The P³¹-bands in the nuclear resonance spectrum show a chemical displacement of −45 ppm (ring-P) and −24 ppm (side chains-P) compared with triphenylphosphate.

EXAMPLE 2

50 parts of acetylacetone and 19 parts of dimethylphosphite are dissolved in 132 parts of absolute benzene. The clear solution is heated to 80° C and is brought to pH 9 by the addition of 1 part of sodium.

There are added at 80°-85° C, with stirring, a further 125 parts of dimethylphosphite and 2 parts of sodium, as a consequence of which a pH-value of 8 − 10 is maintained. After a further 1½ hours' stirring, the whole of the sodium is consumed and the pH-value is 7.2.

After the solvent has been removed by distillation, the excess dimethylphosphite is removed at 0.4 mm at a maximum bath temperature of 80° C.

There are obtained 96 parts (66.7% of theory) of 2-oxo2-methoxy-3,5-dimethyl-3-hydroxy-5-dimethylphosphono-1,2oxaphospholane in the form of a wax-like product. Analysis for $C_8H_{18}O_7P_2$

| calculated | C 33.34% | H 6.30% | P 21.50% |
|---|---|---|---|
| found | 33.2% | 5.9% | 21.70% |

The P³¹NMR absorption bands are at −46.6 ppm and −26.4 ppm compared with triphenylphosphate, corresponding to the P in the ring and in the side chain.

EXAMPLE 3

25 g of acetylacetone are heated at 80° C, with stirring, together with 8 g of diisopropylphosphite and 66 g of benzene. The pH-value is adjusted to 8 by the addition of 0.2 g of sodium. A further 81 g of diisopropylphosphite are added dropwise in 6 hours, with the pH-value being held at 8–10 by the addition of a further 0.7 g of sodium.

Stirring is continued for a further half hour with gentle boiling. The reaction mixture is then cooled to room temperature and neutralised with 3 g of glacial acetic acid. The cloudy solution is filtered until clear and the benzene is distilled off. After removal of the unreacted isopropylphosphite by distillation at 0.4 mm Hg under nitrogen, there remain 27.9 g of 2-oxo-2-isopropoxy3,5-dimethyl-3-hydroxy-5-diisopropylphosphono-1,2-oxaphospholane.

EXAMPLES 4 AND 5

A polyurethane soft foam is produced by mixing together the following materials:

| 100 g | of a polyhydroxyl compound based on polyether having a molecular weight of about 3000 and an OH number of 49, suitable for forming polyurethane soft foam, |
|---|---|
| 1 g | of siloxane-oxyalkylene copolymer, |
| 0.1 g | of tin(II)-octoate, |
| 3.5 g | of water, |
| about 45 g | of toluylene-diisocyanate (80:20 mixture of the 2,4-isomer and the 2,6-isomer), in equimolar amounts relative to polyol, water and flameproofing agent (Index 100), |
| x g | of 2-oxo-2-ethoxy-3,5-dimethyl-3-hydroxy-5-diethylphosphono-1,2-oxaphospholane (compound of the Example 1). |

The foam produced in this manner is tested for its combustibility by the ASTMD Testing Method 1692. For this purpose, a specimen measuring 150 mm × 50 mm × 13 mm is fixed with its 150 × 50 mm surface on a wire gauze. This is bent at one end at an angle of 90° into the vertical position. The specimen is ignited at this end by means of a gas burner: the ignition time is 60 seconds. If the burnt zone is no longer than 125 mm, the foam is designated as self-extinguishing. The length of the burnt zone is given in millimeters. If the specimen burns beyond the 125 mm mark, then it is designated as combustible.

| Amount used x g Flameproofing agent/100 g polyol | none | 6 g | 4 g |
|---|---|---|---|
| a) foaming behaviour | | | |
| creaming time in seconds | 10 | 10 | 12 |
| rising time in seconds | 90 | 85 | 128 |
| time until the foam is no longer sticky, in minutes | 3 | 3 | 2 |
| b) burning behaviour (ASTM D 1692) | | | |
| burnt length in mm | 150 | 45 | 55 |
| burning rate in mm/sec. | 1.8 | 1.0 | 1.5 |

Some foam specimens are also subjected after the flameproofing test to an ageing treatment at 140° C dry and at 90° C wet, after 1, 2, 4 and 7 days.

| Storage conditions 140° C dry | Burnt length in mm with 6 g of flameproofing agent/ 100 g of polyol |
|---|---|
| after 1 day | 95 |
| 2 days | 60 |
| 4 days | 35 |
| 7 days | 25 |
| Storage conditions 90° C wet | |
| after 1 day | 80 |
| 2 days | 70 |
| 4 days | 65 |
| 7 days | 80 |

In the case of reference samples without flameproofing agent the burnt length is always 150 mm.

EXAMPLES 6–8

Under the reaction conditions described in Example 1, 1 mole of acetylacetone is reacted with 2,4 moles of the following phosphites, with the stated oxaphospholanes being obtained:

| Ex. | Phosphite | Product |
|---|---|---|
| 6 | diallylphosphite | 2-oxo-2-alloxy-3,5-methyl-3-hydroxy-5-diallyl-phosphono-1,2-oxaphospholane, |
| 7 | di(β-methoxyethyl)-phosphite | 2-oxo-2-methoxyethoxy-3,5-dimethyl-3-hydroxy-5-di-(methoxyethyl)-phospono-1,2-oxaphospholane, |
| 8 | dibenzylphosphite | 2-oxo-2-benzyloxy-3,5-dimethyl-3-hydroxy-5-dibenzyl-1,2-oxaphospholane. |

The products are obtained as yellowish, highly viscous oils.

EXAMPLES 9 AND 10

If there is reacted, in a manner analogous to that of Example 1, in each case 35 g of diethylphosphite (0.24 mole) with 0.1 mole of 3-methyl-acetylacetone or 3,3-diethylacetylacetone, then there are obtained 2-oxo-2-ethoxy-3,4,5-trimethyl-3-hydroxy-5-diethylphosphono-1,2-oxaphospholane and 2-oxo-2-ethoxy-3,5-dimethyl-4,4-diethyl-3-hydroxy-5-diethylphosphono-1,2-oxaphospholane, respectively.

EXAMPLE 11

50 g of benzoylacetone (0.3 mole) in 150 ml of absolute benzene is heated to 80° C; there are then added 6 g of diethylphosphite and 0.1 g of sodium.

There is then added dropwise, with gentle boiling, 99 g of diethylphosphite. The pH-value is maintained between 8 and 10 by the addition in small portions of 1.5 g of sodium, with further processing being carried out as described in Example 1. There is obtained 70 g (59.5% yield) of 2-oxo-2-ethoxy-3-phenyl-5-methyl-3-hydroxy-5-diethylphosphono-1,2-oxaphospholane.

EXAMPLE 12

104 g of acetoacetic acid is dissolved in 300 ml of absolute benzene. After the addition of 20 g of diethylphosphite, the reaction mixture is heated to 80° C, and an addition is initially made to it of 0.4 g of sodium.

There is subsequently added dropwise, with gentle boiling, 256 g of diethylphosphite, with the pH-value being maintained at 8–10 with 1.9 g of sodium. After a further 30 minutes, the reaction mixture is cooled to room temperature and neutralised with 3 ml of glacial acetic acid.

The benzene is distilled off in vacuo. After removal of the unreacted diethylphosphite at about 0.1 mm at a maximum temperature of 90° C, there remains 178 g of 2-oxo-2-ethoxy-3-methyl-3-hydroxy-5-ethoxy-5-diethylphosphono-1,2-oxaphospholane in the form of a viscous oil, the $P^{31}$ NMR-spectrum of which displays an absorption band at 42 ppm compared with triphenylphosphate.

We claim:

1. A flameproofed composition comprising a polymer selected from the group consisting of a polyurethane and an epoxide resin and from 2 to 30 percent by weight of the polymer of a compound of the formula I

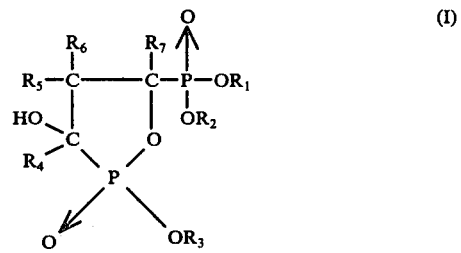

wherein
$R_1$ and $R_2$ each independently represent alkyl having 1–4 carbon atoms, cyclohexyl, aralkyl having 7 or 8 carbon atoms, alkoxyalkyl having 3–6 carbon atoms, halogenoalkyl having 2–3 carbon atoms, or alkenyl having 3–5 carbon atoms, $R_3$ is identical to $R_1$ or $R_2$, $R_4$ is alkyl having 1–4 carbon atoms, or phenyl, $R_5$ and $R_6$ each independently represent hydrogen or alkyl having 1–4 carbon atoms, and $R_7$ represents hydrogen, alkyl having 1–4 carbon atoms, alkoxy having 1–4 carbon atoms, or phenyl.

2. A composition according to claim 1 wherein the compound of formula I
    $R_1$ and $R_2$ each independently represent alkyl having 1–4 carbon atoms, cyclohexyl, benzyl, allyl or alkoxyethyl having 3–5 carbon atoms; $R_3$ is identical to $R_1$ or $R_2$; $R_4$ and $R_7$ each independently represent alkyl having 1–4 carbon atoms or phenyl; and $R_5$ and $R_6$ represent hydrogen.

3. A composition according to claim 1 wherein the compound of formula I is 2-oxo-2-ethoxy-3,5-dimethyl-3-hydroxy-5-diethylphosphono-1,2-oxaphospholane.

4. A compositin according to claim 1 where the compound of formula I is 2-oxo-2-methoxy-3,5-dimethyl-3-hydroxy-5-dimethylphosphono-1,2-oxaphospholane.

5. A composition according to claim 1 wherein the compound of formula I is 2-oxo-2-isopropoxy-3,5-dimethyl-3-hydroxy-5-diisopropylphosphono-1,2-oxaphospholane.

6. A composition according to claim 1 wherein the polymer is selected from the group consisting of a foamed polyurethane and a foamed epoxide resin.

7. A compound of the formula I

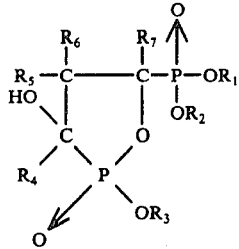

wherein $R_1$ and $R_2$ each independently represent methyl, propyl, butyl, cyclohexyl, aralkyl having 7 or 8 carbon atoms, alkoxyalkyl having 3 – 6 carbon atoms, halogenoalkyl having 2 – 3 carbon atoms, or alkenyl havig 3 – 5 carbon atoms, $R_3$ is identical to $R_1$ or $R_2$, $R_4$ is alkyl having 1 – 4 carbon atoms, or phenyl, $R_5$ and $R_6$ each independently represent hydrogen or alkyl having 1 – 4 carbon atoms, and $R_7$ represents hydrogen, alkyl having 1 – 4 carbon atoms, alkoxy having 1 – 4 carbon atoms, or phenyl.

8. A compound of the formula I of claim 7, wherein $R_1$ and $R_2$ each independently represent methyl, propyl, butyl, cyclohexyl, benzyl, alkoxyethyl having 3 – 5 carbon atoms, or allyl, $R_3$ is identical to $R_1$ or $R_2$, $R_4$ and $R_7$ represent alkyl hving 1 – 4 carbon atoms, or phenyl, and $R_5$ and $R_6$ represent hydrogen.

9. A compound of the formula I of claim 7, wherein $R_1$ and $R_2$ have the same meaning.

10. The compound according to claim 7, 2-oxa-2-methoxy3,5-dimethyl-3-hydroxy-5-dimethylphosphono-1,2-oxaphospholane.

11. The compound according to claim 7, 2-oxa-2-isopropoxy-3,5-dimethyl-3-hydroxy-5-diisopropylphosphono1,2-oxaphospholane.

* * * * *